(12) United States Patent
Ansley et al.

(10) Patent No.: US 9,486,552 B1
(45) Date of Patent: Nov. 8, 2016

(54) AIR TREATMENT APPLIANCE

(71) Applicant: Prolitec Inc., Milwaukee, WI (US)

(72) Inventors: Matthew Ansley, Muskego, WI (US);
Nathan Sward, Milwaukee, WI (US);
Andrew Williams, Elm Grove, WI (US); Harold Wikel, Muskego, WI (US)

(73) Assignee: Prolitec Inc., Milwaukee, WI (US)

( * ) Notice: Subject to any disclaimer, the term of this patent is extended or adjusted under 35 U.S.C. 154(b) by 0 days.

(21) Appl. No.: 14/918,375

(22) Filed: Oct. 20, 2015

(51) Int. Cl.
*A61L 9/14* (2006.01)
*B01F 3/04* (2006.01)

(52) U.S. Cl.
CPC .............. *A61L 9/14* (2013.01); *B01F 3/04063* (2013.01)

(58) Field of Classification Search
CPC .. B01F 3/04; B01F 3/04007; B01F 3/04063; B01F 3/04049; B01F 3/04021
USPC ................................. 261/76, 78.2, 72.1, 118
See application file for complete search history.

(56) References Cited

U.S. PATENT DOCUMENTS

| | | | |
|---|---|---|---|
| RE24,291 E | 3/1957 | Goodyer | |
| 3,339,094 A | 8/1967 | Shopsky | |
| 3,545,894 A | 12/1970 | Lovitz | |
| 3,825,374 A | 7/1974 | Kondo | |
| 3,830,596 A | 8/1974 | Kondo | |
| 4,007,238 A | 2/1977 | Glenn | |
| 4,162,876 A | 7/1979 | Kolfertz | |
| 4,190,046 A | 2/1980 | Virag | |
| 4,595,564 A | 6/1986 | Spector et al. | |
| 4,877,378 A | 10/1989 | Saggers | |
| 5,213,484 A | 5/1993 | Hashimoto et al. | |
| 5,533,497 A | 7/1996 | Ryder | |
| 5,554,012 A | 9/1996 | Itakura | |
| 6,007,307 A | 12/1999 | Sonoda | |
| 6,379,124 B1 | 4/2002 | Lai | |
| 6,405,944 B1 | 6/2002 | Benalikhoudja | |
| 7,036,800 B2 | 5/2006 | Ellis | |
| 7,178,743 B2 * | 2/2007 | Clarke, III | ............ B05B 7/2416 239/304 |
| 7,363,737 B2 | 4/2008 | Benalikhoudja | |
| 7,377,493 B2 | 5/2008 | Thomas | |
| 7,493,898 B2 | 2/2009 | King | |
| 7,581,718 B1 | 9/2009 | Chang | |

(Continued)

FOREIGN PATENT DOCUMENTS

| | | |
|---|---|---|
| EP | 0 135 390 A2 | 3/1985 |
| EP | 0 753 664 A1 | 1/1997 |

(Continued)

*Primary Examiner* — Robert A Hopkins
(74) *Attorney, Agent, or Firm* — Seed IP Law Group LLP

(57) ABSTRACT

An air treatment appliance is provided which includes an appliance housing and a removable cartridge received therein. The removable cartridge contains a liquid compound to be aerosolized and has a cartridge outlet through which the aerosolized compound is discharged during operation. A pump is provided to supply air to the removable cartridge to generate the aerosolized compound from the liquid compound contained in the removable cartridge, and a controller is provided for controlling the pump to supply the air to the removable cartridge to generate and discharge the aerosolized compound from the appliance. In some instances, the appliance housing includes a base, a cover, and an inner sub-housing coupled to the base to collectively define a passageway with an air outlet positioned to discharge a flow of air across a path of the aerosolized compound discharged from the cartridge outlet during operation.

19 Claims, 9 Drawing Sheets

(56) References Cited

U.S. PATENT DOCUMENTS

| | | |
|---|---|---|
| 7,712,683 B2 | 5/2010 | Robert et al. |
| 7,930,068 B2 | 4/2011 | Robert et al. |
| 7,950,630 B2 | 5/2011 | Curien |
| 8,006,698 B2 | 8/2011 | Boehm et al. |
| 8,562,914 B2 | 10/2013 | Slutz et al. |
| 8,596,264 B2 | 12/2013 | Sommer |
| 8,602,396 B1 | 12/2013 | V et al. |
| 8,855,827 B2 | 10/2014 | Weening et al. |
| 8,876,086 B2 | 11/2014 | Burke et al. |
| 9,162,004 B1 | 10/2015 | Ansley et al. |
| 2005/0047923 A1 | 3/2005 | Li et al. |
| 2006/0219814 A1 | 10/2006 | Benalikhoudja |
| 2006/0237090 A1 | 10/2006 | Benalikhoudja |
| 2009/0010778 A1 | 1/2009 | Wang |
| 2009/0078793 A1 | 3/2009 | Nelson et al. |
| 2010/0086418 A1 | 4/2010 | Sevy |
| 2013/0049236 A1 | 2/2013 | Garon et al. |
| 2015/0076716 A1 | 3/2015 | Roemburg et al. |
| 2015/0298147 A1 | 10/2015 | Ansley et al. |
| 2015/0300345 A1 | 10/2015 | Ansley et al. |

FOREIGN PATENT DOCUMENTS

| | | |
|---|---|---|
| GB | 726916 A | 3/1955 |
| GB | 2365081 A | 2/2002 |

* cited by examiner

AIR TREATMENT APPLIANCE

BACKGROUND

1. Technical Field

The present disclosure relates generally to air treatment appliances and, more specifically, to air treatment appliances including a removable cartridge containing a liquid compound to be diffused or aerosolized and released into a space to be treated.

2. Description of the Related Art

Air treatment appliances in the past have had the ability to dispense scent compounds or other compounds throughout the atmosphere of desired spaces but can suffer from various drawbacks or deficiencies. For example, some air treatment appliances and removable cartridges thereof may be overly complex, costly and/or suffer from other deficiencies or drawbacks, such as, for example, discharging diffused liquid with less than ideal characteristics, or the cartridges being susceptible to leakage, tampering, fouling and/or contamination.

BRIEF SUMMARY

The air treatment appliances and removable cartridges and other components thereof shown and described herein provide efficient form factors that are robust, efficient, and particularly effective at treating spaces with diffused or aerosolized compound from a liquid source in a non-obtrusive manner.

At least one embodiment of an air treatment appliance may be summarized as including: a removable cartridge containing a liquid compound to be aerosolized and including a cartridge outlet through which the aerosolized compound is discharged; a pump operatively coupled to the removable cartridge to supply air to the removable cartridge to generate the aerosolized compound from the liquid compound contained in the removable cartridge; a controller operatively coupled to the pump for controlling the pump to supply the air to the removable cartridge to generate the aerosolized compound and discharge the aerosolized compound from the cartridge outlet; and an appliance housing that accommodates the removable cartridge, the pump and the controller within an internal cavity thereof.

The appliance housing may include a base, a cover coupled to the base to define the internal cavity, and an inner sub-housing located within the internal cavity. The inner sub-housing may be coupled to the base to collectively define a passageway having an air outlet that is positioned to discharge a flow of air across a path of the aerosolized compound discharged from the cartridge outlet during operation. The inner sub-housing may include a discharge nozzle which defines a terminal end of the passageway and includes the air outlet, and the discharge nozzle may be oriented to discharge the flow of air oblique to the path of the aerosolized compound discharged from the cartridge outlet. The inner sub-housing may further include a tongue having an alignment groove for receiving a stem of the removable cartridge which contains the cartridge outlet and for assisting in aligning the cartridge outlet and the path of the aerosolized compound with the air outlet of the discharge nozzle of the inner sub-housing. The air treatment device may further include a fan device positioned within a compartment of the appliance housing formed between the base and the inner sub-housing, the fan device including a fan intake and a fan outlet arranged to draw in air from the compartment and move air through the passageway leading to the air outlet that is positioned to discharge the flow of air across the path of the aerosolized compound discharged from the cartridge outlet during operation. At least some functional electronics of the controller may be located within the compartment of the appliance housing formed between the base and the inner sub-housing, and the fan intake may be arranged to draw in air from across said functional electronics of the controller.

The air treatment appliance may further include a power adapter unit coupleable to a power outlet of a wall, and the base of the appliance housing may define a power adapter cavity or alcove that is sized and shaped to accommodate the power adapter unit and to conceal the power adapter unit when the air treatment appliance is fixed to the wall.

The air treatment appliance may further include a pump mount arrangement that couples the pump to the appliance housing. The pump mount arrangement may include a pump bracket and a plurality of groupings of isolators arranged in different planes to suppress vibrations of the pump in multiple directions. The pump bracket may suspend the pump within a pump cavity located at a lower end of the appliance housing. The base and the cover of the appliance housing may collectively define a pump cavity to accommodate the pump, and the air treatment appliance may further include a sound deadening or muffling device that is positioned within the pump cavity to substantially fill a void between the pump and the appliance housing. The sound deadening or muffling device may comprise a compliant material formed in a shape that corresponds to the void between the pump and the appliance housing.

In some instances, the removable cartridge may include a base receptacle having one or more alignment indentations formed in a side thereof, and the base of the appliance housing may include a back and opposing sidewalls with one or more corresponding alignment projections which nest with the alignment indentations of the removable cartridge.

The air treatment appliance may further include a conduit assembly that couples an air outlet of the pump to an air inlet of the removable cartridge. The conduit assembly may include a conduit fitting and a conduit with one or more corrugated sections to facilitate routing of the conduit between the air outlet of the pump and the air inlet of the removable cartridge. The conduit fitting may include a seal member having a plurality of resilient projections at a terminal end thereof for sealingly engaging the air inlet of the removable cartridge, a stem for mating with a terminal end of the conduit, and a locking device for locking the conduit fitting and the conduit to the removable cartridge. In some instances, a unitary single-piece conduit may be provided comprising one or more corrugated sections to facilitate routing of the conduit between the air outlet of the pump and the air inlet of the removable cartridge, a plurality of resilient projections at a terminal end thereof for sealingly engaging the air inlet of the removable cartridge, and a locking device for locking the conduit to the removable cartridge. The locking device may include a grip portion for manipulating the locking device and for assisting in installing the removable cartridge in the appliance housing and removing the removable cartridge from the appliance housing.

The air treatment appliance may further include a supplemental power source and a caddy for the supplemental power source for removably positioning the supplemental power source within the appliance housing. The caddy may include finger grips projecting from an end thereof for assisting in removal of the supplemental power source from the appliance housing.

The base of the appliance housing may include a back having an arrangement of mounting apertures for securing the appliance housing to a wall, or alternatively to an appliance stand. Upper and lower edges of the back and a peripheral edge of each of the opposing sidewalls of the base of the appliance housing may include a plurality of indentations to receive corresponding projections of the cover to join the base and the cover together without separate fasteners.

The appliance housing may further include a lock assembly coupled to the cover for locking the cover directly to one or more catch members formed integrally with the base of the appliance housing. The lock assembly may include a retaining ring having an upstanding tab to assist in installation and removal of the retaining ring from a corresponding shaft of the lock assembly which supports a rotatable latch for locking the cover to the base via the catch members. The cover may include a separate sub-cover for concealing the lock assembly. The sub-cover may be removably secured to the cover via an arrangement of integral coupling members and a flexible lanyard.

Each of the cover and the base of the appliance housing may include a respective lanyard mount formed integrally therewith, and the air treatment appliance may further include a lanyard connecting the cover to the base via the lanyard mounts.

At least one embodiment of a cartridge assembly for an air treatment appliance may be summarized as including: a receptacle containing a liquid compound to be aerosolized within an interior thereof; and a cap assembly coupled to the receptacle. The cap assembly may include a cap, a venturi insert, and a base attached together without welds or separate fasteners to define an air inlet chamber on one side of the venturi insert, a venturi outlet passage on the other side of the venturi insert in fluid communication with the interior of the receptacle, and an aerosol outlet chamber partitioned from the interior of the receptacle by the base and in fluid communication with an outlet of the cap through which aerosolized compound generated by the venturi insert is discharged during operation.

The cap may include a plurality of columnar projections and the base may include a corresponding plurality of apertures to mate with the columnar projections of the cap to attach the base to the cap and secure the venturi insert therebetween. Each columnar projection may comprise a polygonal shaped cross-section and may taper with increasing distance away from a proximal end of the columnar projection. The base at each corresponding aperture may comprise a cylindrical profile that interfaces with each respective columnar projection at a plurality of discrete areas of contact to securely attach the base to the cap. The base may include a perimeter having at least a portion that is correspondingly shaped to an interior profile of the cap such that at least a portion of a peripheral edge of the base assists in holding the base in position within the cap via a friction or interference fit. The base may be wedged in the cap to prevent separation of the base from the cap and to maintain the venturi insert in position between the cap and the base. A mouth of the receptacle may also prevent the base from separating from the cap. The cap may be fixedly coupled to the receptacle to prevent non-destructive disassembly of the cartridge. The cap may include a seal integrally formed therewith and may be fixedly coupled to the receptacle with the seal engaging a mouth of the receptacle. The base may include a chimney to allow the aerosolized compound to move from the interior of the receptacle to the aerosol outlet chamber and may include a drain aperture to allow a condensed portion of the aerosolized compound to drain out of the cap through the base into the receptacle to be aerosolized again. The base may mate with the cap to define a circumferential ledge which underlies a peripheral edge region of the venturi insert. The cap may include a plurality of outlet nozzles for discharging the aerosolized compound from one or more of multiple outlets. At least one of the plurality of outlet nozzles may include a barrier integrally formed in the cap which isolates an outlet passage of the outlet nozzle from the aerosol outlet chamber until removed. The cap may include an internal partition defining a venturi receptacle that is sized and shaped to insertably receive the venturi insert. The internal partition may also define at least a portion of the air inlet chamber and at least a portion of the aerosol outlet chamber. The cap may include a lock feature formed integrally therewith for locking an air conduit to the cap for receiving a flow of air for generating the aerosolized compound. The venturi insert may include a conduit that extends through the base and into the receptacle for withdrawing the liquid compound from the receptacle to be aerosolized by the venturi insert.

DETAILED DESCRIPTION

In the following description, certain specific details are set forth in order to provide a thorough understanding of various disclosed embodiments. However, one skilled in the relevant art will recognize that embodiments may be practiced without one or more of these specific details. In other instances, well-known devices, structures and techniques associated with air treatment appliances (or liquid diffusion devices), components thereof and related methods of diffusing or aerosolizing a compound from a liquid source may not be shown or described in detail to avoid unnecessarily obscuring descriptions of the embodiments. For example, embodiments of the air treatment appliances and removable cartridges disclosed herein may include or incorporate aspects or features of known appliances and associated components and control methods thereof. Examples of known air treatment appliances, components and aspects thereof and related methods are shown and described in U.S. Pat. Nos. 7,712,683, 7,930,068 and 8,855,827, all of which are incorporated herein by reference in their entirety.

Unless the context requires otherwise, throughout the specification and claims which follow, the word "comprise" and variations thereof, such as "comprises" and "comprising," are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Figure 1:
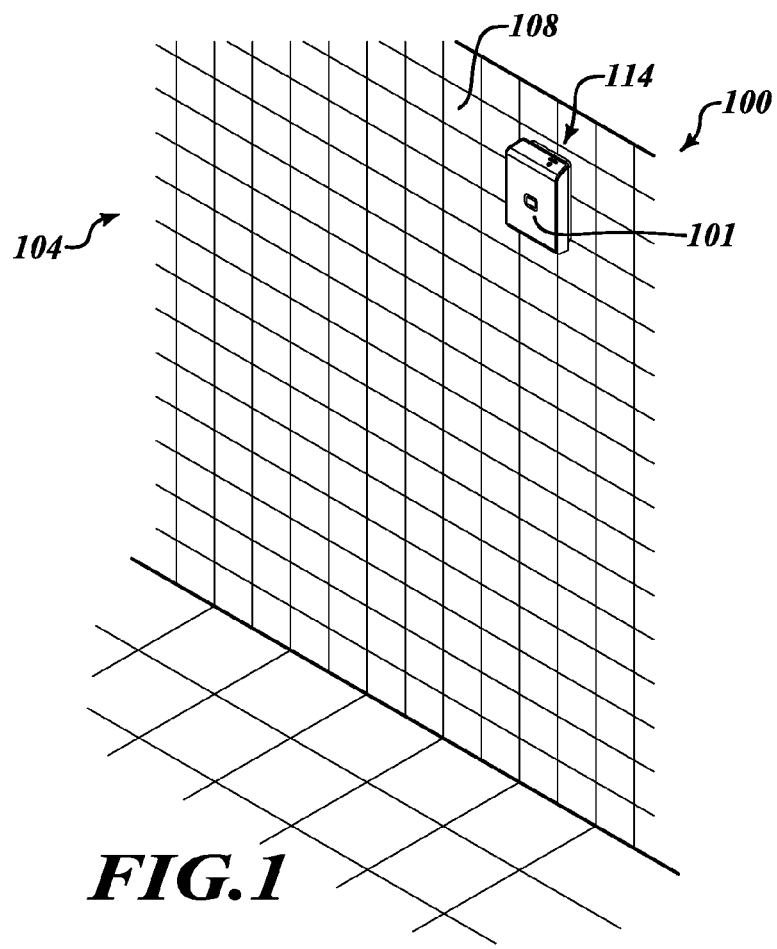
FIG. 1 is an isometric view of an air treatment appliance attached to a wall in a space, such as a public restroom, for treating the space with a scent compound or other compound diffused or aerosolized from a liquid.
Figure 2:
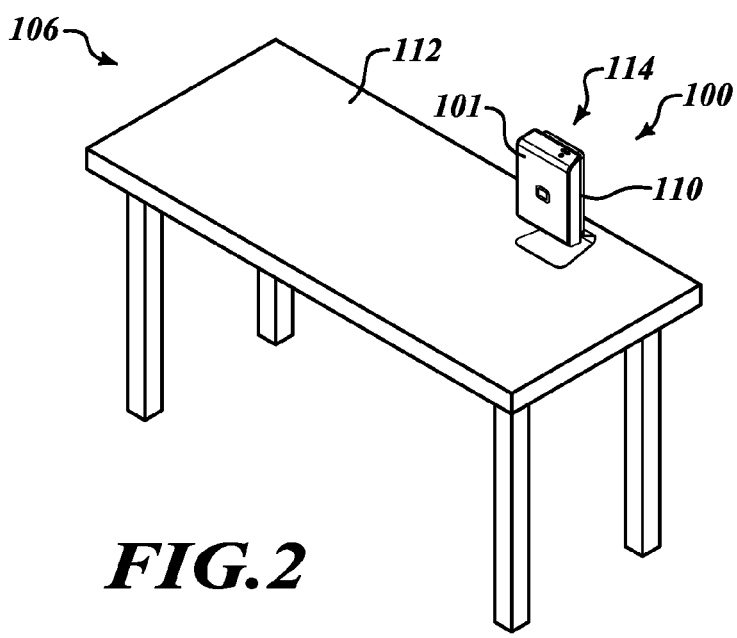
FIG. 2 is an isometric view of the air treatment appliance attached to a stand and resting on a table in a space, such as a residential living space or commercial workspace, for treating the space with a scent compound or other compound diffused or aerosolized from a liquid.

With reference to FIGS. 1 and 2, the present disclosure relates generally to air treatment appliances 100 and more specifically to air treatment appliances 100 including a removable cartridge 102 (FIG. 3) containing a liquid compound to be diffused or aerosolized and released into a space 104, 106 to be treated (also referred to as liquid diffusion devices or apparatuses), and to components thereof and related methods of discharging a diffused or aerosolized compound into the space 104, 106 from a liquid source.

Figure 3:
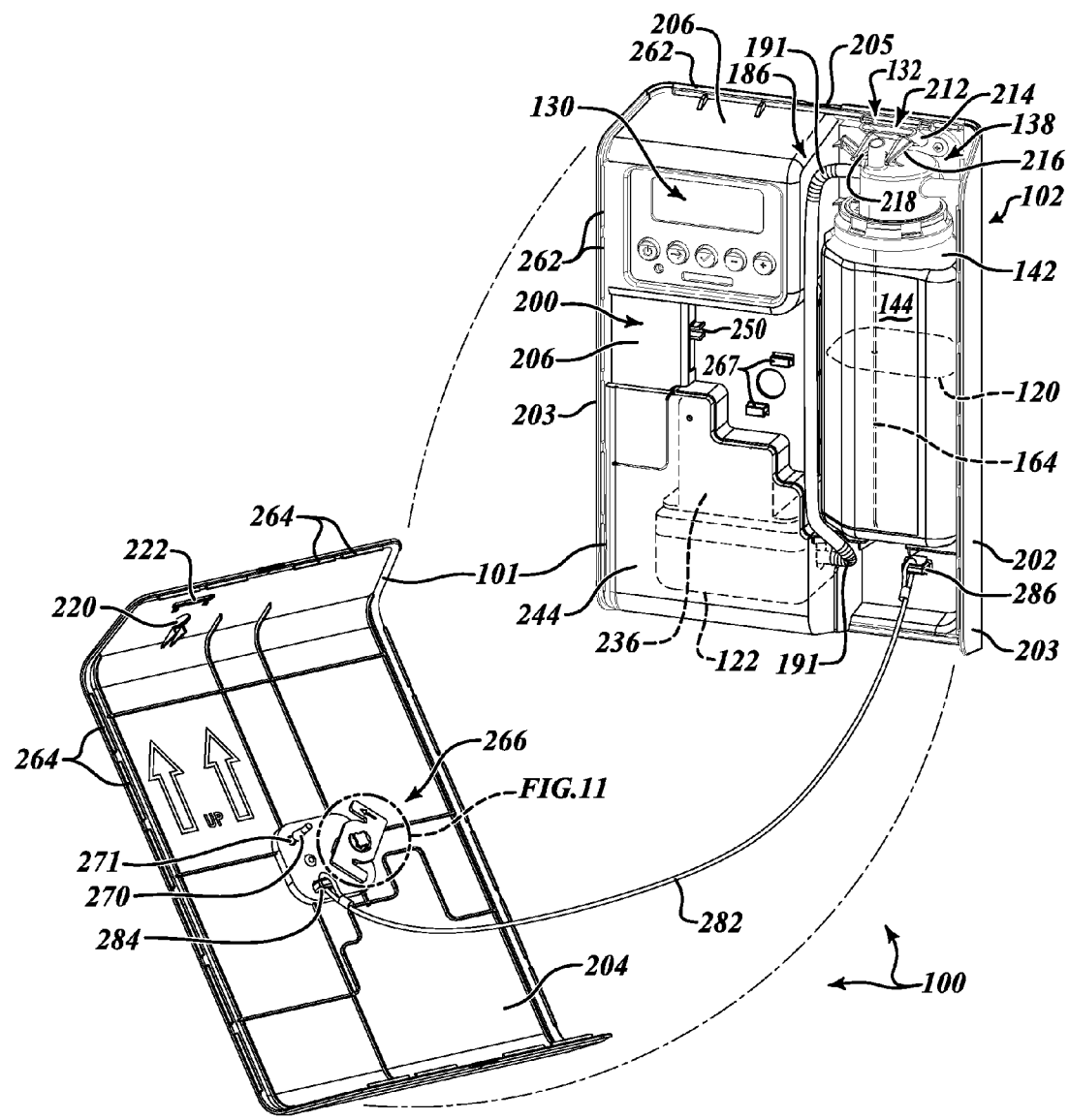
FIG. 3 is a front isometric view of the air treatment appliance of FIGS. 1 and 2 with a cover thereof removed to reveal internal components and features of the air treatment appliance, including a removable cartridge that is configured to generate and discharge a scent compound or other compound diffused or aerosolized from a liquid when air is forced to move therethrough.

As shown in FIG. 1, the air treatment appliance 100 may be attached to a wall 108 in a space 104, such as a public restroom, for treating the space 104 with a scent compound or other compound diffused or aerosolized from a liquid source. As shown in FIG. 2, the air treatment appliance 100 may be attached to a stand 110 to rest on a table 112 or other structure in a space 106, such as a residential living space or commercial workspace, for treating the space 106 with a scent compound or other compound diffused or aerosolized from a liquid source. For this purpose, an outlet 114 is provided in the appliance 100 to permit a diffused or aerosolized compound generated from the liquid 120 (FIG. 3) within the cartridge 102 to be discharged into the environment or space 104, 106 surrounding the appliance 100. With reference to FIG. 3, the removable cartridge 102 within the appliance 100 is coupled to an outlet of a source of pressurized air (e.g., pump assembly 122) to enable pressurized air to be selectively passed through the cartridge 102 as described herein to diffuse or aerosolize the liquid 120 contained therein.

Within the present disclosure, the terms atomize and diffuse are used in their various forms interchangeably. They are intended to refer to generally the same action, that being the dispersion of liquid into very small particle sizes (preferably but not limited to one micron or less in size) and releasing the particles into the atmosphere of a generally enclosed space. Discharging diffused liquid with particularly small particles helps ensure that the liquid to be dispersed remains airborne long enough to effectively treat the space 104, 106.

One approach to providing small particle sizes is to incorporate a dispersion or gas-liquid mixing location adjacent an expansion chamber. The mixed gas and liquid combination may contain particles of greater than desirable size. Allowing this mix to remain resident within the expansion chamber prior to release into the treated space 104, 106 will allow larger particles to precipitate out of the mix. Structures that the gas and liquid mixture impinge upon may also assist in the collection of these larger particles and leave only the desired predominantly smaller sized particles to be released. The expansion chamber may be maintained at a positive pressure with respect to the atmospheric pressure within the space 104, 106 to be treated, so that the gas and liquid mix will be injected from the appliance 100 into the space 104, 106. Alternatively, the expansion chamber may generally be maintained at the atmospheric pressure of the space 104, 106 to be treated with the flow of gas (e.g., air) through the chamber, providing the impetus for movement of the gas and liquid mix from the device into the space 104, 106 to be treated.

Within the context of this disclosure, diffusion or aerosolizing also generally refers to a process or method of dispersing a liquid without destroying the integrity of the liquid compound. While some degree of reactivity between the gas (e.g., air) and the liquid may be desirable, diffusion generally does not change the nature of the liquid, unlike heating or the application of electrical energy into the liquid to diffuse the liquid.

The air treatment appliances 100, removable cartridges 102 and other components described herein may be used to provide or introduce a pleasant or soothing scent (or some other type of liquid that may be used as an airborne treatment or compound) into the air space 104, 106 of a room or other enclosed space. The particular liquid 120 to be dispensed by the diffusion device is contained within the removable cartridge 102. Other possible types of liquids that may be dispersed may include decontamination agents, insecticides, insect repellents, and many different types of liquids that may be desirably dispersed within an enclosed space 104, 106. The present disclosure is not limited to a particular type or nature of liquid 120 to be dispersed, but is intended to encompass any desirable airborne liquid treatments that are preferably dispersed within an enclosed space 104, 106 to be effective. The term enclosed space, as used herein, refers to any volume of space within which the atmospheric turnover is sufficiently slow to permit the dispersed liquid to have its desired effect within the space. Larger spaces, such as concert halls, casinos, lobbies, etc., may have one or more openings into the space and still have the desired characteristics to permit treatment with a diffused liquid. Other spaces may be preferably fully enclosed to permit treatment by the selected liquid. In other cases, the liquid used for treatment may preferably be used in a sealed space, for maximum effectiveness or for safety reasons. Within the scope of the present disclosure, it is not intended to limit the nature, size or configuration of the space to be treated except as may be appropriate for the liquid used to treat the space and the nature of treatment desired within the space.

With reference to FIG. 3, and according to the illustrated embodiment, a controller 130 is provided and is configured to permit adjustment of the timing and/or pressure level of the pressurized air generated by a pump assembly 122 that is ultimately directed into and passes through the cartridge 102. In some instances, the operating pressure may be relatively low, such as, for example, less than about 2 psi gauge pressure or about 1.5 psi gauge pressure. Within the cartridge 102, the pressurized air is directed to atomize the liquid 120 contained therein and to aid in the dispersion of the atomized liquid into the air space to be treated.

In some instances, it may be desirable to have an indirect route from the point of actual atomization of the liquid and an outlet 132 through which a portion of the atomized particles exit from the cartridge 102 and ultimately from the appliance 100. As will be described in greater detail elsewhere, embodiments of the removable cartridges 102 described herein provide an atomization zone where liquid 120 from the cartridge 102 and pressurized air meet and are mixed. In addition, the cartridges 102 may also provide an expansion chamber or chambers within the cartridge 102 where the atomized liquid is retained until a portion of the atomized liquid is allowed to exit the cartridge 102 and the host appliance 100. As described in greater detail elsewhere, the cartridges 102 may combine storage of the liquid 120 to be diffused, an atomization structure to transform the liquid 120 into an airborne concentration, an expansion chamber or chambers, and optionally a tortuous path or passage towards the outlet 132 of the cartridge 102 and the outlet 114 of the appliance 100 (which may be one and the same).

With reference to FIGS. 1 through 3, one example embodiment of an air treatment appliance 100 is illustrated and includes an appliance housing 101 and a removable cartridge 102 accommodated therein. As previously discussed, the appliance 100 is configured to treat a space 104, 106 with a diffused or aerosolized compound generated by a flow of air moving through the cartridge 102 which is entrained with liquid particles from liquid 120 contained in the cartridge 102.

As shown in FIG. 3, the removable cartridge 102 may include a cap assembly 138 and a receptacle 142 coupled together to define a fluid receptacle having an internal cavity 144, which is partially filled with the liquid 120 to be diffused. In some instances, the cap assembly 138 and the receptacle 142 may be fixedly coupled together to prevent non-destructive disassembly of the removable cartridge 102, making it effectively tamperproof. This may be desirable to prevent users from refilling and reusing a spent cartridge that may be ineffective or less effective in treating the space 104, 106 due to fouling or build-up of residue within the cartridge 102 from prior use.

As an example, and with reference now to FIGS. 4 through 8, the cap assembly 138 and the receptacle 142 may be provided with interlocking structures 146, 148 that snap or otherwise couple together in a manner that prevents non-destructive disassembly of the cartridge 102. A seal 150, such as an o-ring seal or other seal, may be provided between a cap 140 of the cap assembly 138 and a mouth 152 of the receptacle 142 near the interlocking structures 146, 148 to provide a liquid tight seal when the cartridge 102 is assembled. In some embodiments, the cap 140 may include a seal 150 integrally formed therewith via an overmolding, multi-shot injection or other suitable process for engaging the mouth 152 of the receptacle 142 when the cartridge 102 is assembled. In this manner, the liquid 120 to be diffused may be prevented from leaking from the cartridge 102 at an interface between the cap 140 and the receptacle 142. Upon depletion of the liquid 120, the cartridge 102 may be removed and replaced with a like cartridge 102 for continued treatment of the environment or space 104, 106 surrounding the appliance 100, and the depleted cartridge 102 may be discarded as an intact unit or collected for refurbishment purposes.

With continued reference to FIGS. 4 through 8, an air inlet 154 may be provided in the cap 140 to receive a flow of pressurized air from the pump assembly 122 (FIG. 3) during operation and the cartridge outlet 132 may be provided in the cap 140 for discharging the diffused or aerosolized compound generated by the cartridge 102 during operation. According to the illustrated embodiment of the cartridge 102 shown in FIGS. 4 through 8, the internal components and structures thereof provide, among other things, a flow path through the cartridge 102 from the air inlet 154 to the cartridge outlet 132, as represented by the arrows labeled 156a-156e in FIGS. 7 and 8. When installed in the appliance 100, the air inlet 154 is coupled to a source of pressurized air (e.g., pump assembly 122) such that the air may be periodically forced through the cartridge 102 as generally represented by the arrows labeled 156a-156e in FIGS. 7 and 8 to combine with the liquid 120 (shown in FIG. 3) and to exit as a gas-liquid mixture comprising particularly small liquid particles carried by the air, referred to generally herein as a diffused or aerosolized compound, or simply an aerosol or diffused liquid.

Figure 7:
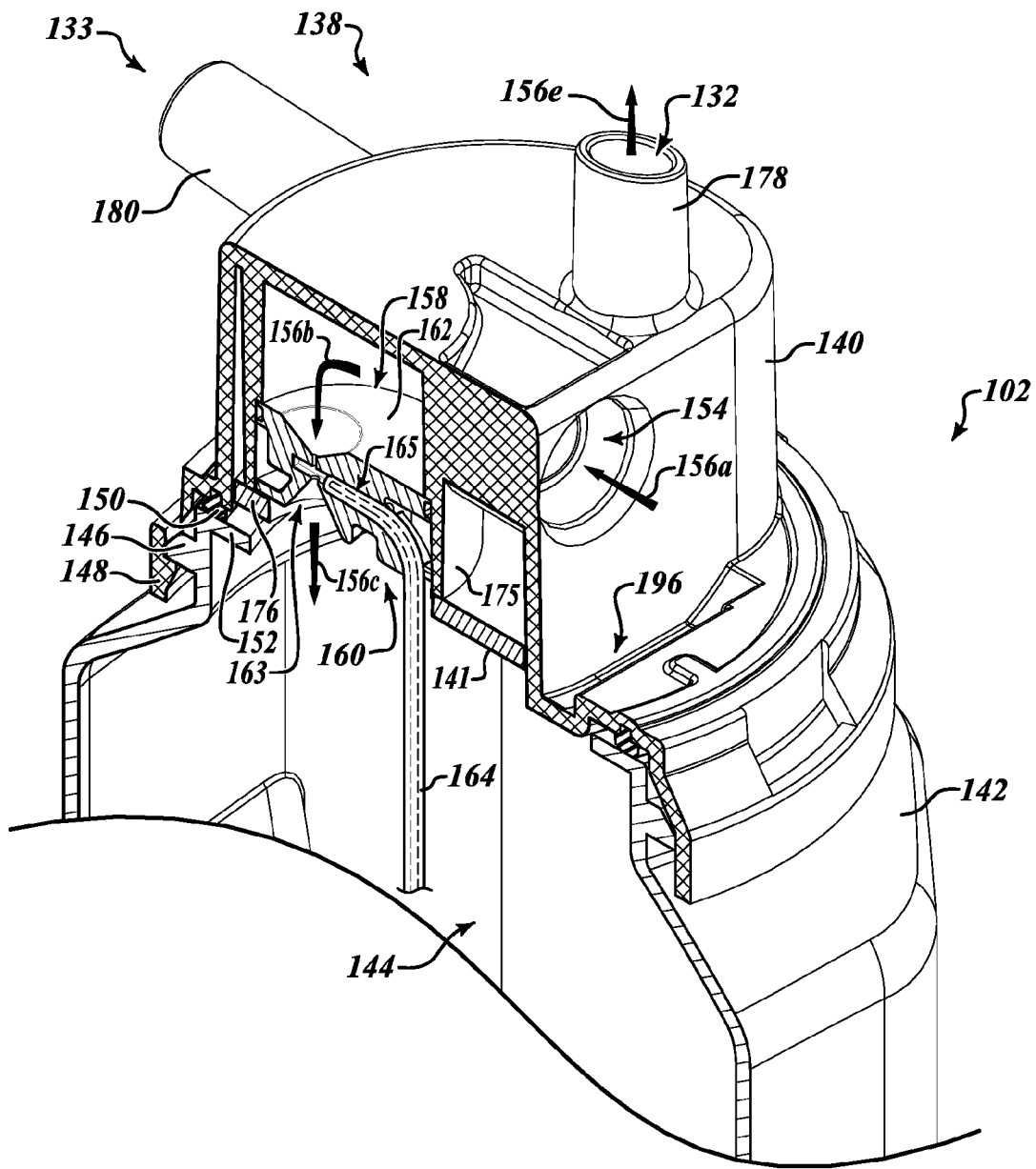
FIG. 7 is a partial isometric cross-sectional view of the removable cartridge of FIG. 3.
Figure 8:
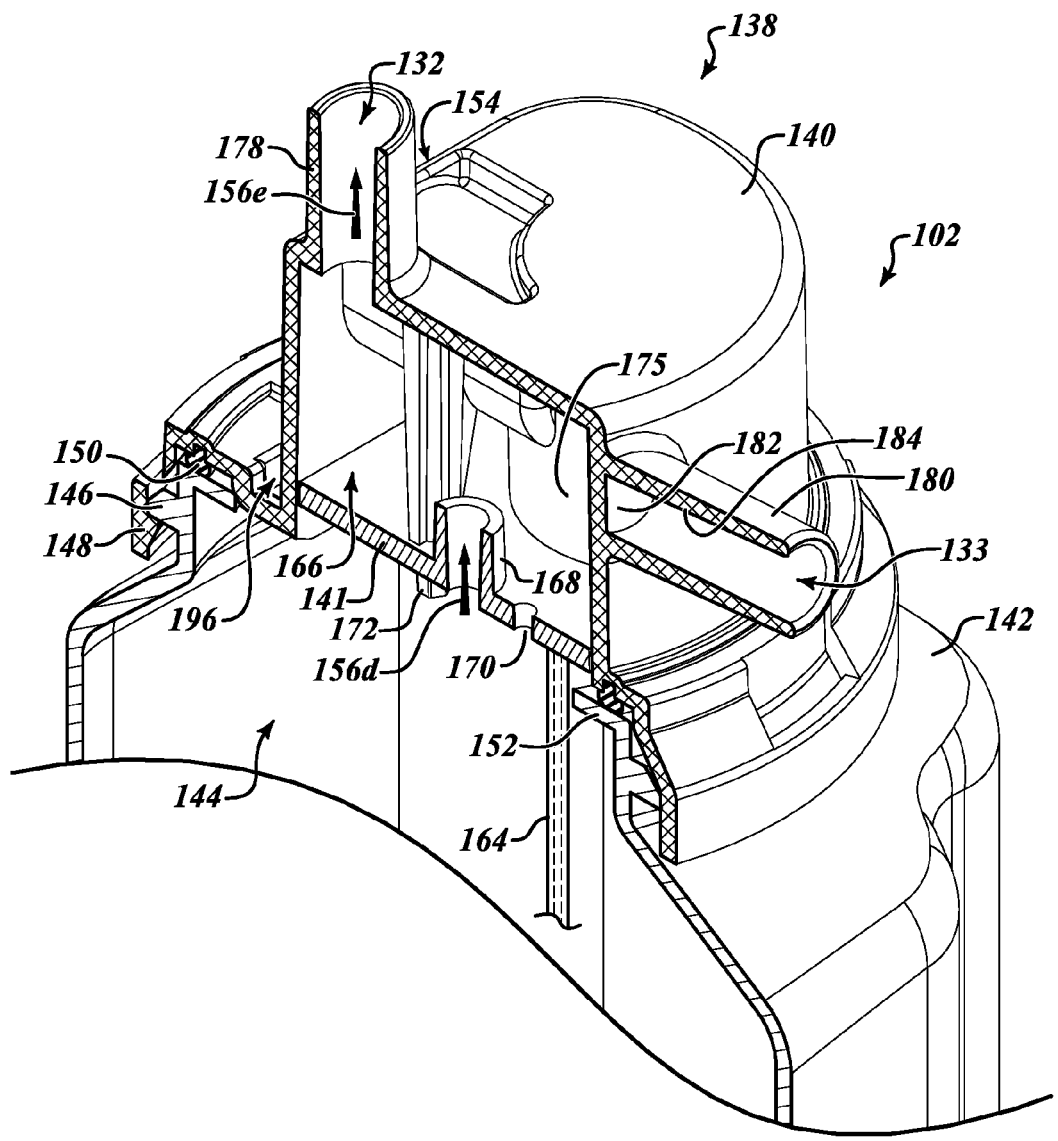
FIG. 8 is another partial isometric cross-sectional view of the removable cartridge of FIG. 3.

As shown in FIGS. 7 and 8, the pressurized gas enters the cartridge 102 through the air inlet 154 at a side of the cap 140 and then flows into air inlet chamber 158 and through a venturi insert 160 provided within the cap 140, which includes a venturi body 162 and an associated venturi conduit 164 for drawing liquid 120 into the moving air stream, to generate a gas-liquid mixture that is discharged into the internal cavity 144 of the receptacle 142 en route to an aerosol outlet chamber 166 via a chimney structure 168 and ultimately to the cartridge outlet 132. More particularly, the pressurized air enters the cartridge 102 through the air inlet 154 at a side of the cap 140, as represented by the arrow labeled 156a in FIG. 7, and then moves into air inlet chamber 158 and through the venturi insert 160, as represented by the arrow labeled 156b in FIG. 7. As the air flows through the venturi insert 160, liquid 120 from the receptacle 142 is drawn into the air stream via the venturi conduit 164 and venturi body 162 to create a gas-liquid mixture comprising atomized liquid (also referred to herein as diffused or aerosolized compound) that is then discharged into the internal cavity 144 of the receptacle 142 above the remaining liquid 120, as represented by the arrow labeled 156c in FIG. 7. The diffused or aerosolized compound is directed out of the venturi body 162 toward a surface of the remaining liquid 120 in the receptacle 142 and at least some of the diffused or aerosolized compound impacts and recombines with the remaining fluid 120 in the receptacle 142 to be reintroduced into the air stream by the venturi insert 160. Some of the diffused or aerosolized compound may also collect on the exposed interior surfaces of the receptacle 142, or otherwise precipitate out of the gas and atomized liquid, and rejoin the liquid 120 in the receptacle 142 to be reintroduced into the gas stream by the venturi insert 160. Some other of the diffused or aerosolized compound may be driven or forced into the aerosol outlet chamber 166 through a chimney structure 168, as represented by the arrow labeled 156d in FIG. 8. From there some of the diffused or aerosolized compound proceeds to exit the cartridge 102 through the cartridge outlet 132, as represented by the arrow labeled 156e in FIG. 8. In making this journey, the liquid particle size distribution of the diffused or aerosolized compound may be refined such that only particularly fine particles are successfully discharged from the cartridge 102, with relatively larger particles collecting on one or more surfaces of the internal structures and components of the cartridge 102, or otherwise precipitating out of the gas, for rejoining with the remaining liquid 120 in the receptacle for reintroduction into the air stream that is forced through the venturi body 162 during operation. For example, some of the diffused or aerosolized compound residing in the aerosol outlet chamber 166 may collect on the exposed interior surfaces of the aerosol outlet chamber 166, or otherwise precipitate out of the gas and atomized liquid, and rejoin the liquid 120 in the receptacle 142 through a drain aperture 170 which provides fluid communication between the aerosol outlet chamber 166 and the internal cavity 144 of the receptacle 142.

As shown in FIG. 7, the venturi body 162 may include a tube receiving passage 165 to receive one end of the venturi conduit 164 and to position an outlet of the venturi conduit 164 in fluid communication with a flow passage 163 of the venturi body 162 such that the liquid 120 may be drawn into the path of the pressurized air as it is accelerated via the flow passage 163 of the venturi body 162. The flow passage 163 of the venturi body 162 may comprise a convergent entrance, a narrow throat, a side port for introduction of the liquid, and a divergent outlet which are configured to accelerate the flow of air, draw in the liquid 120 through the side port and discharge the diffused mixture of air and liquid into the internal cavity 144 of the receptacle 142. The size and shape of the flow passage 163 may be configured based on characteristics of the air flow, the geometry of an air supply conduit 186 (FIG. 3) that provides the air flow, and the volume and velocity of air required to effectively draw liquid 120 up the venturi conduit 164 and atomize liquid 120 via the venturi body 162.

Figure 4:
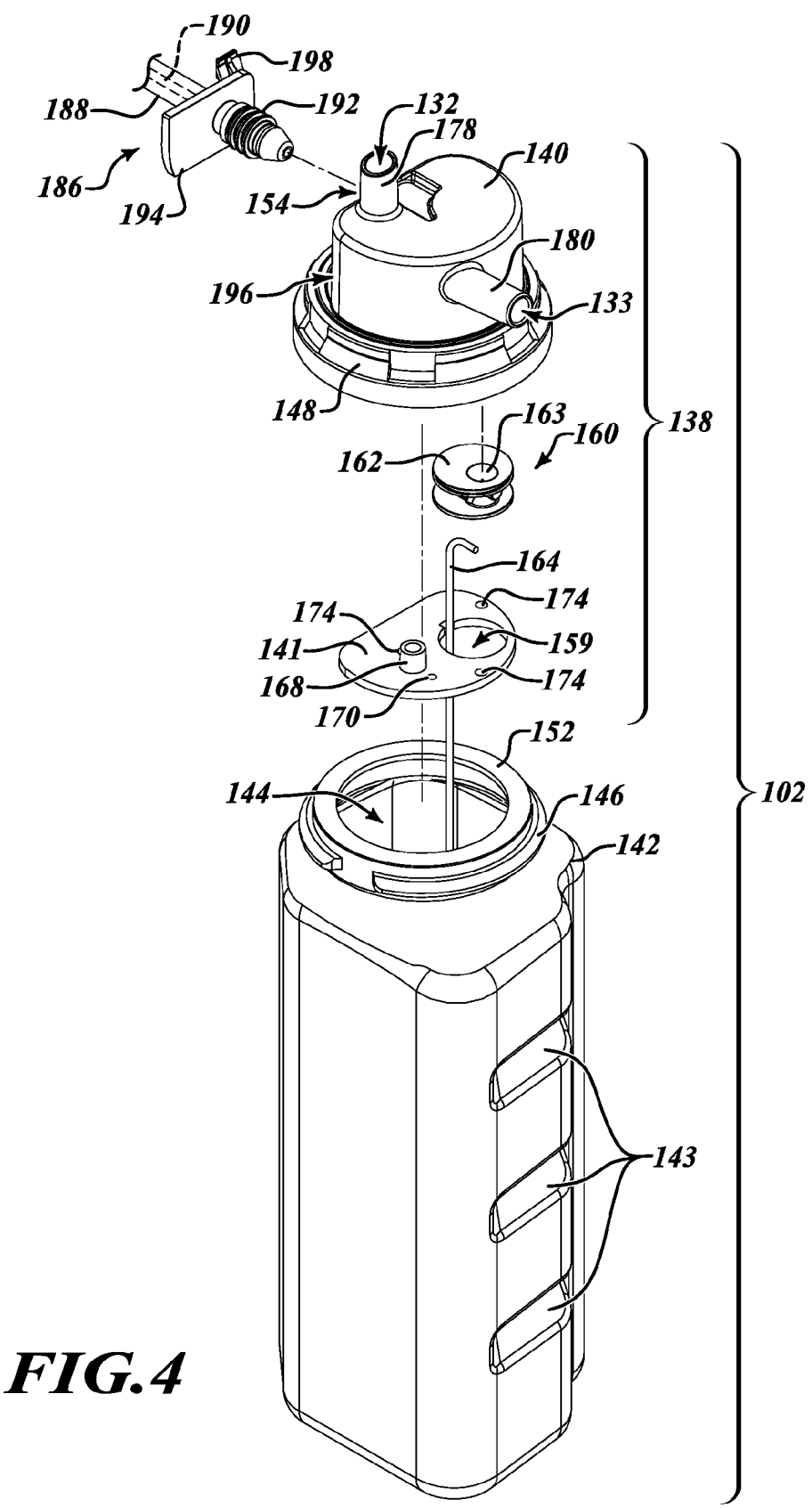
FIG. 4 is an isometric exploded view of the removable cartridge shown in FIG. 3.

FIG. 4 provides an exploded view of the removable cartridge 102 for additional clarity. Again, the removable cartridge 102 includes the receptacle 142 for containing the liquid 120 to be aerosolized and the cap assembly 138 which is coupleable to the receptacle 142 to form the cartridge 102. The cap assembly 138 includes the cap 140, the venturi insert 160 and a cap base 141 that attach together without welds or separate fasteners to define, among other things, the air inlet chamber 158 on one side of the venturi insert 160, as shown FIG. 7, a venturi outlet passage 159 passing through the cap base 141 on the other side of the venturi insert 160, as shown in FIG. 5, and the aerosol outlet chamber 166 which is partitioned from the internal cavity 144 of the receptacle 142 by the cap base 141 and in fluid communication with the outlet 132 of the cap 140 through which the diffused or aerosolized compound generated by the venturi insert 160 is discharged during operation, as shown in FIG. 8.

With reference to FIG. 8, the cap 140 may include a plurality of columnar projections 172 and the cap base 141 may include a corresponding plurality of apertures 174 (FIG. 4) to mate with the columnar projections 172 of the cap 140 to attach the cap base 141 to the cap 140 and secure the venturi insert 160 therebetween. Each columnar projection 172 of the cap 140 may have a polygonal shaped (e.g., hexagon, pentagon, etc.) cross-section and may taper with increasing distance away from a proximal or root end of the columnar projection 172. The cap base 141 at each corresponding aperture 174 may have a cylindrical profile that interfaces with each respective columnar projection 172 at a plurality of discrete areas of contact to securely attach the cap base 141 to the cap 140 without welds or separate fasteners. In some instances, the cap base 141 may include a perimeter having at least a portion that is correspondingly shaped to an interior profile of the cap 140 such that at least a portion of a peripheral edge of the cap base 141 assists in holding the cap base 141 in position within the cap 140 via a friction or interference fit. In some instances, the cap base 141 may be wedged in the cap 140 to prevent separation of the cap base 141 from the cap 140 and to maintain the venturi insert 160 in position between the cap 140 and the cap base 141. In addition, as can be appreciated from FIGS. 7 and 8, the mouth 152 of the receptacle 142 may also prevent the cap base 141 from separating from the cap 140 when the cap assembly 138 is attached to the receptacle 142 to form the cartridge 102.

Figures 5, 6:
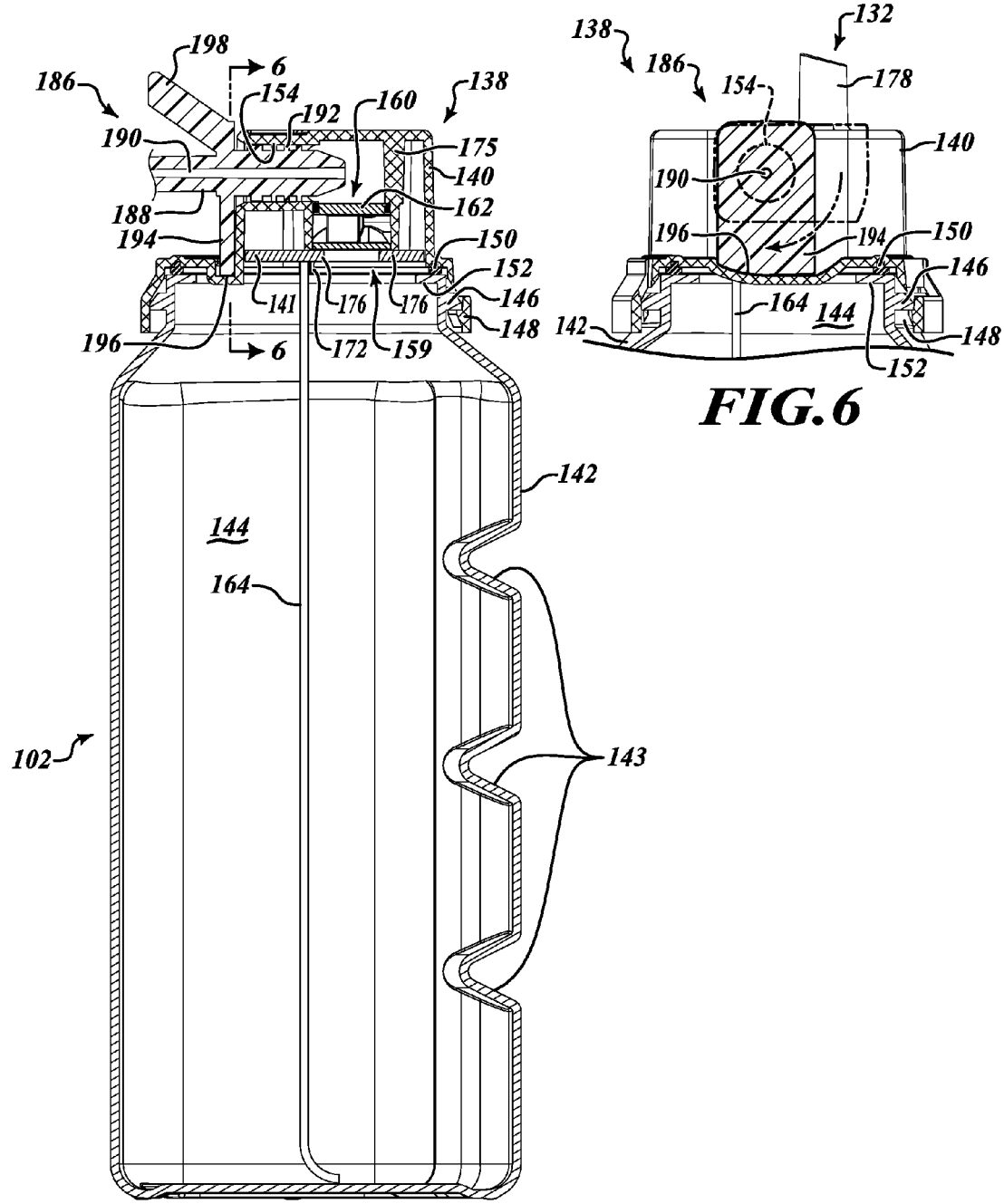
FIG. 5 is a cross-sectional view of the removable cartridge shown in FIG. 3.
FIG. 6 is a partial cross-sectional view of the removable cartridge shown in FIG. 3 taken along the line 6-6 in FIG. 5.

With reference now to FIG. 5, the cap 140 may include an internal partition 175 that defines at least a portion of a venturi receptacle that is sized and shaped to insertably receive the venturi insert 160. The internal partition 175 may also define at least a portion of the air inlet chamber 158 and at least a portion of the aerosol outlet chamber 166. Furthermore, the cap base 141 may mate with internal partition 175 of the cap 140 to provide a circumferential ledge 176 that underlies a peripheral edge region of the venturi body 162 of the venturi insert 160 to retain the venturi insert 160 in position between the cap 140 and the cap base 141.

With reference again to FIGS. 7 and 8, the cap 140 may also be provided with a plurality of outlet nozzles 178, 180 for discharging the aerosolized matter from one or more of corresponding outlets 132, 133 in different directions. At least one of the plurality of outlet nozzles 178, 180 may include a barrier 182 integrally formed in the cap 140 which isolates an outlet passage 184 of the outlet nozzle 180 from the aerosol outlet chamber 166 until the barrier 182 is removed. To use the alternate outlet 133, a user need only remove the barrier 182, such as via drilling or another suitable process, and optionally plug the other outlet 132 or outlets when provided.

With reference to FIGS. 3 through 6, the cartridge 102 may include or otherwise operate in conjunction with an air supply conduit 186 the couples an outlet of the pump assembly 122 to the air inlet 154 of the cap 140. The air supply conduit 186 may be provided as an assembly of parts, or, in one particularly advantageous embodiment, a single integrally formed member as illustrated in the figures. The air supply conduit 186 may include a tubular body 188 having an internal air passage 190 extending therethrough. The tubular body 188 may have one or more corrugated sections 191 to facilitate routing of the air supply conduit 186 between the air outlet of the pump assembly 122 and the air inlet 154 of the cap 140. The air supply conduit 186 may further comprise a plurality of resilient projections 192 at a terminal end thereof for sealingly engaging the air inlet 154 of the cap 140. The air supply conduit 186 may also include a locking device 194 for locking the air supply conduit 186 to the cap 140 via a corresponding lock feature 196 formed integrally in the cap 140. For example, the locking device 194 may comprise a tab which is insertable in a corresponding lock feature 196 in the form of a lock cavity by rotating the locking device 194 from an unlocked position to a locked position after coupling the air supply conduit 186 to the inlet 154 of the cap 140. The locking device 194 may further include a grip portion 198 for manipulating the locking device 194 and for assisting in installing the cartridge 102 in the appliance housing 101 and removing the cartridge 102 from the appliance housing 101.

Further details of the air treatment appliance 100 and components thereof will now be described with reference to FIG. 3. As previously described, the air treatment appliance 100 includes a removable cartridge 102 containing a liquid 120 to be aerosolized and discharged through a cartridge outlet 132, a pump assembly 122 operatively coupled to the removable cartridge 102 to supply air to the removable cartridge 102 to generate the aerosolized compound from the liquid 120, a controller 130 operatively coupled to the pump assembly 122 for controlling the pump assembly 122 to supply the air to the removable cartridge 102 to generate the aerosolized compound and discharge the aerosolized compound from the cartridge outlet 132, and an appliance housing 101 that accommodates the removable cartridge 102, the pump assembly 122 and the controller 132 within an internal cavity 200 thereof. As shown in FIG. 3, the appliance housing 101 includes a base 202, a cover 204 coupleable to the base 202 to define the internal cavity 200, and an inner sub-housing 206 located within the internal cavity 200.

Figure 9:
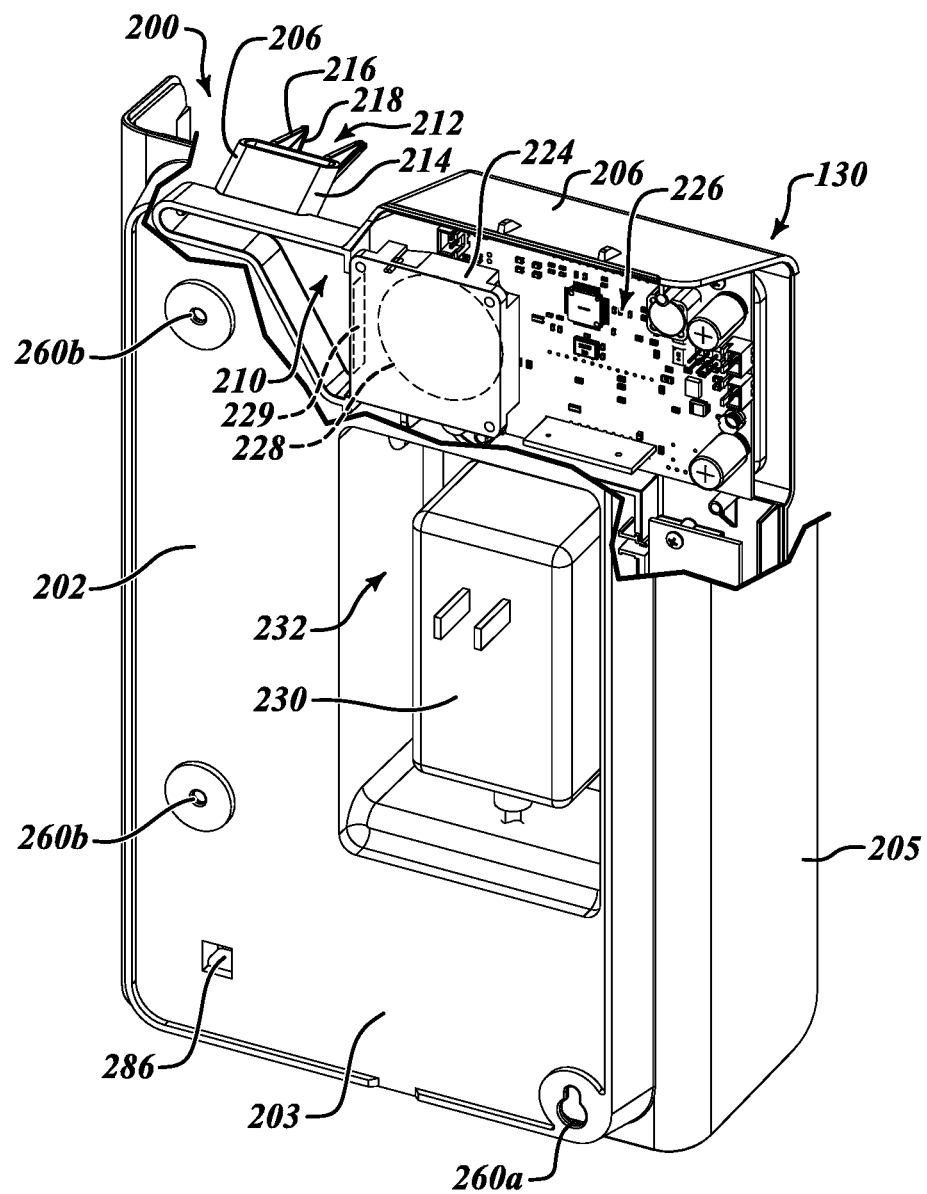
FIG. 9 is a rear isometric view of the air treatment appliance of FIGS. 1 and 2 with a portion of a back of the appliance cut away to reveal additional internal components and features thereof.

Advantageously, and with reference to FIG. 9, the inner sub-housing 206 may be coupled to the base 202 to collectively define at least a portion of a passageway 210 having an air outlet 212 that is positioned to discharge a flow of air across a path of the aerosolized compound that is discharged from the cartridge outlet 132 during operation. The inner sub-housing 206 may include a discharge nozzle 214 which defines a terminal end of the passageway 210 and includes the air outlet 212. According to the illustrated embodiment, the discharge nozzle 214 is oriented to discharge the flow of air oblique to the path of the aerosolized compound discharged from the cartridge outlet 132 (which also serves as the appliance outlet 114). In this manner, the discharged flow of air from the air outlet 212 may assist in carrying the diffused or aerosolized compound into the space to be treated, and further dispersing the compound for more effective treatment of the space.

With continued reference to FIG. 9, the inner sub-housing 206 may further include a tongue 216 having an alignment groove 218 for receiving the stem or nozzle 178 of the removable cartridge 102 which contains the cartridge outlet 132 and for assisting in aligning the cartridge outlet 132 and path of the aerosolized compound with the air outlet 212 of the discharge nozzle 214 of the inner sub-housing 206. In this manner, the inner sub-housing 206 can assist in aligning the cartridge outlet 132 and the air outlet 212 of the discharge nozzle 214 relative to each other and also with respect to corresponding apertures 220, 222 that may be provided in the cover 204 for enabling the aerosolized compound and flow of air intersecting the same to be discharged from the air treatment appliance 100.

With continued reference to FIG. 9, the air treatment appliance 100 may further include a fan device 224 positioned within a compartment 226 of the appliance housing 101 that is formed between the base 202 and the inner sub-housing 206. The fan device 224 may include a fan intake 228 and a fan outlet 229 arranged to draw in air from the compartment 226 and move air through the passageway 210 leading to the air outlet 212 that is positioned to discharge the flow of air across the path of the aerosolized compound discharged from the cartridge outlet 132 (FIG. 3) during operation. Moreover, at least some of the functional electronics of the controller 130 may be located within the compartment 226 of the appliance housing 101 formed between the base 202 and the inner sub-housing 206, and the fan intake 228 may be arranged to draw in air from across said functional electronics of the controller 130. In this manner, the fan device 224 may assist in cooling functional electronics of the controller 130 while also warming or heating the discharged aerosolized compound, which may assist in effectively treating the space.

With continued reference to FIG. 9, the air treatment appliance 100 may further include a power unit 230 for connecting the appliance 100 to a power outlet of a wall to which the appliance 100 may be mounted. For this purpose, the base 202 of the appliance housing 101 may define a power adapter cavity 232 that is sized and shaped to accommodate the power adapter unit 230 and to conceal the power adapter unit 230. The base 202 of the appliance housing 101 may include a back 203 and opposing sides 205 and the power adapter cavity 232 may be formed directly into the back 203 of the base 202 between the opposing sides 205 to form an alcove for the power adapter unit 230.

Figure 10:
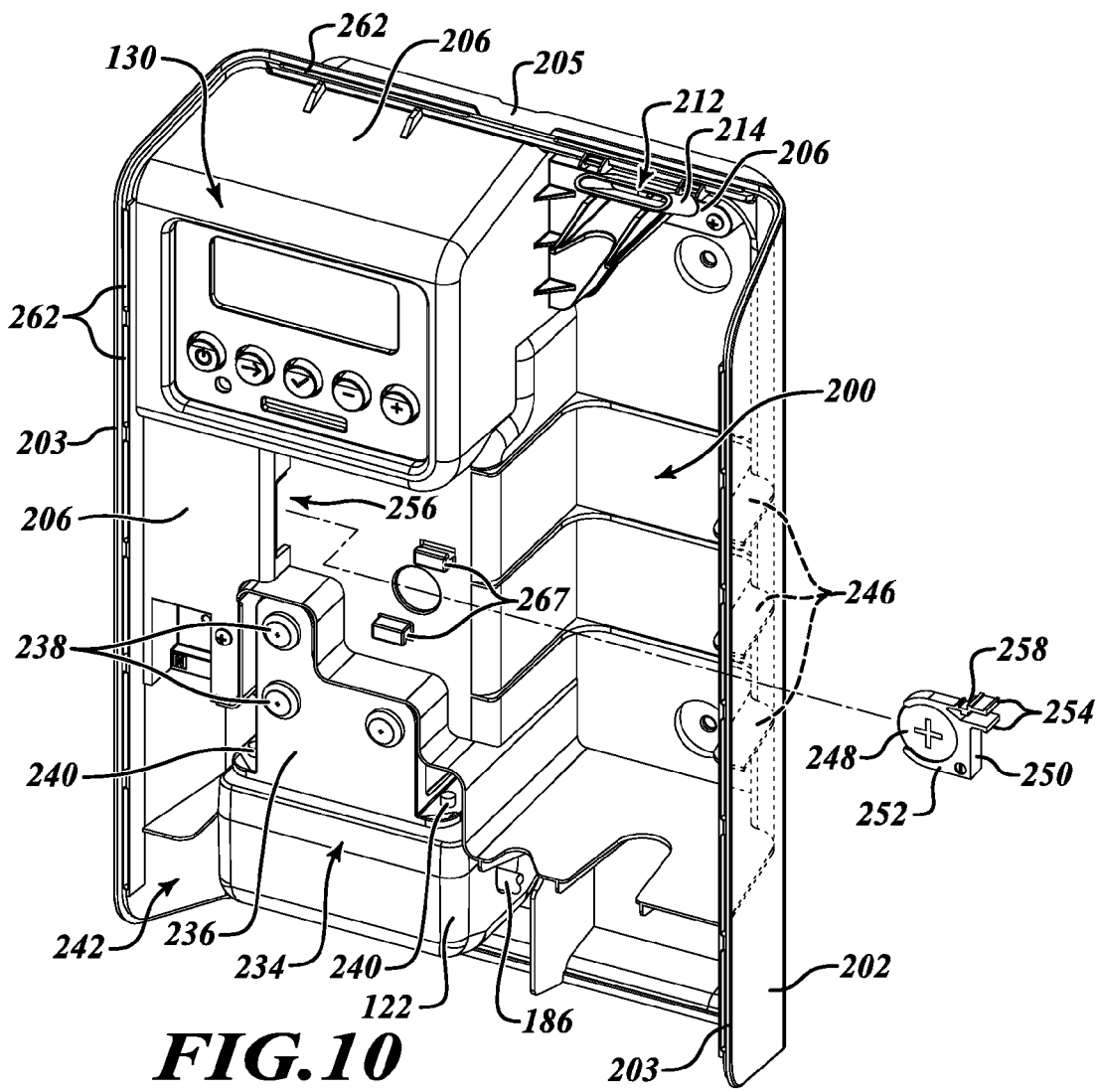
FIG. 10 is another front isometric view of the air treatment appliance of FIGS. 1 and 2 with the cover and other components removed to reveal yet further internal components and features of the air treatment appliance.

With reference now to FIG. 10, the air treatment appliance 100 may further include a pump mount arrangement 234 that couples the pump assembly 122 to the appliance housing 101. The pump mount arrangement 234 may include a pump bracket 236 and a plurality of groupings of isolators 238, 240 arranged in different planes (e.g., orthogonal planes) to suppress vibrations of the pump assembly 122 in multiple directions. For example, as shown in FIG. 10, the pump bracket 236 may be L-shaped and a first grouping of isolators 238 may couple a vertical leg of the bracket 236 to the appliance housing 101 with respective axes of the isolators 238 aligned generally normal to a front face of the appliance 100. A second grouping of isolators 240 may couple a horizontal leg of the bracket 236 to the appliance housing 101 with respective axes of the isolators 240 aligned generally parallel to a front face of the appliance 100. Collectively, the groupings of isolators 238, 240 may suppress vibrations of the pump assembly 122 in multiple directions, such as in orthogonal directions. This may suppress vibrations otherwise associated with the pump assembly 122 and allow the appliance 100 to run quieter.

As can be appreciated in FIG. 10, the pump bracket 236 may suspend the pump assembly 122 within a pump cavity 242 located at a lower end of the appliance housing 101, which is collectively defined by the base 202 and the cover 204. Advantageously, a sound deadening or muffling device 244 may be positioned within the pump cavity to substantially fill a void between the pump assembly 122 and the appliance housing 101, as shown in FIG. 3. The sound deadening or muffling device 244 may comprise a compliant material that is formed in a shape that corresponds to the void between the pump assembly 122 and the appliance housing 101 such that there is substantially no empty space in the vicinity of the pump assembly 122. This may further dampen or suppress vibrations from the pump assembly 122 and muffle any sounds emanating from the pump assembly 122.

As shown in FIG. 4, the receptacle 142 of the cartridge 102 may include one or more indentations 143 formed in a side thereof which may provide additional rigidity to the receptacle 142 as well as provide indexing features for installing the cartridge 102 in the appliance housing 101 in the proper position. As such, the base 202 of the appliance housing 101 may include one or more corresponding alignment projections 246, as shown in FIG. 10, which are configured to nest with the indentations 143 of the receptacle 142 of the cartridge 102 to assist in receiving the cartridge 102 within the appliance housing 101.

With reference to FIG. 10, the air treatment appliance 100 may include a supplemental power source 248, such as a disc battery, and may include a caddy 250 for the supplemental power source 248. The caddy 250 may be removably coupleable to the appliance housing 101 to position the supplemental power source 248 within the appliance housing 101 and enable replacement of the power source 248 (e.g., battery) as needed. The caddy 250 may include a body 252 shaped to accommodate the power source 248 and may include finger grips 254 projecting from an end thereof for assisting in the removal of the supplemental power source 248 from a corresponding cavity 256 of the appliance housing 101 and installation of a replacement power source. The finger grips 254 may be resilient and/or flexible and may include a latch element 258 for securing the caddy 250 to the appliance housing 101 when installed.

With reference to FIG. 9, the back 203 of the appliance housing 101 may include an arrangement of mounting apertures 260a, 260b for securing the appliance housing 101 to a wall 108, as shown in FIG. 1, or alternatively to an appliance stand 110 for resting the appliance 100 on a table 112 or other structure, as shown in FIG. 2. Advantageously, when installing the appliance 100 to a wall, the power adapter unit 230 may be secured to a power outlet and the appliance housing 101 may be hung from some of the mounting apertures 260a including keyhole slots on the wall 108 in a position to conceal the power adapter unit 230 within the power adapter cavity 232. The appliance 100 may then be further secured to the wall from an interior of the appliance 100 using fasteners through the remaining mounting apertures 260b. The appliance 100 may then be programmed and locked to prevent access to the mounting fasteners and removal of the appliance 100 and/or other tampering.

With reference to FIG. 3, upper and lower edges of the back 203 and a peripheral edge of each of the opposing sides 205 of the base 202 of the appliance housing 101 may include a plurality of indentations 262 to receive corresponding projections 264 provided along a periphery of the cover 204 to join the base 202 and the cover 204 together without separate fasteners. The base 202 and the cover 204 may snap together in a friction fit, interference fit or snap fit. When assembled, the cover 204 may be locked to the base 202 to prevent unintended access to the interior of the appliance 100. For this purpose, the appliance housing 101 may further include a lock assembly 266 coupled to the cover 204 for locking the cover 204 directly to one or more catch members 267 formed integrally with the base 202 of the appliance housing 101. The lock assembly 266 and in particular the keyhole face of the lock assembly 266 may be concealed by a separate sub-cover 268 (FIG. 12) which may removably secured to the cover 204 via an arrangement of integral coupling members 269 (e.g., detents, snaps, clips, etc.), and a flexible lanyard 270 which may secured to a corresponding aperture 271 in the cover 204.

Figure 11:
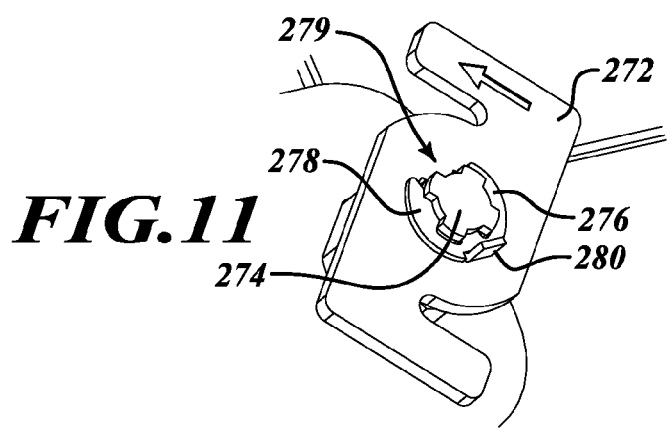
FIG. 11 is an enlarged view of a lock assembly of the air treatment appliance taken from FIG. 3.

With reference to FIG. 11, the lock assembly 266 may comprise a rotatable latch 272 that is secured to a shaft 274 of the lock assembly by a retainer 276. The retainer 276 may include a body 278 that resembles a conventional snap ring, circlip or other split retaining ring but which further includes an upstanding tab 280 projecting from the body 278 to assist in installation and removal of the retainer 276. The upstanding tab 280 may project from the body 278 at a peripheral edge opposite a split or gap 279 in the ring structure.

With reference back to FIG. 3, when the cover 204 is unlocked and removed from the base 202, such as, for example, when installing or servicing the appliance 100, the cover 204 may remain attached to the base 202 via a lanyard 282 that is secured at opposing ends to lanyard mounts 284, 286 formed integrally with the cover 204 and the base 202. In this manner, the risk of misplacing and/or inadvertently damaging the cover 204 during maintenance or otherwise may be minimized or eliminated.

Figure 12:
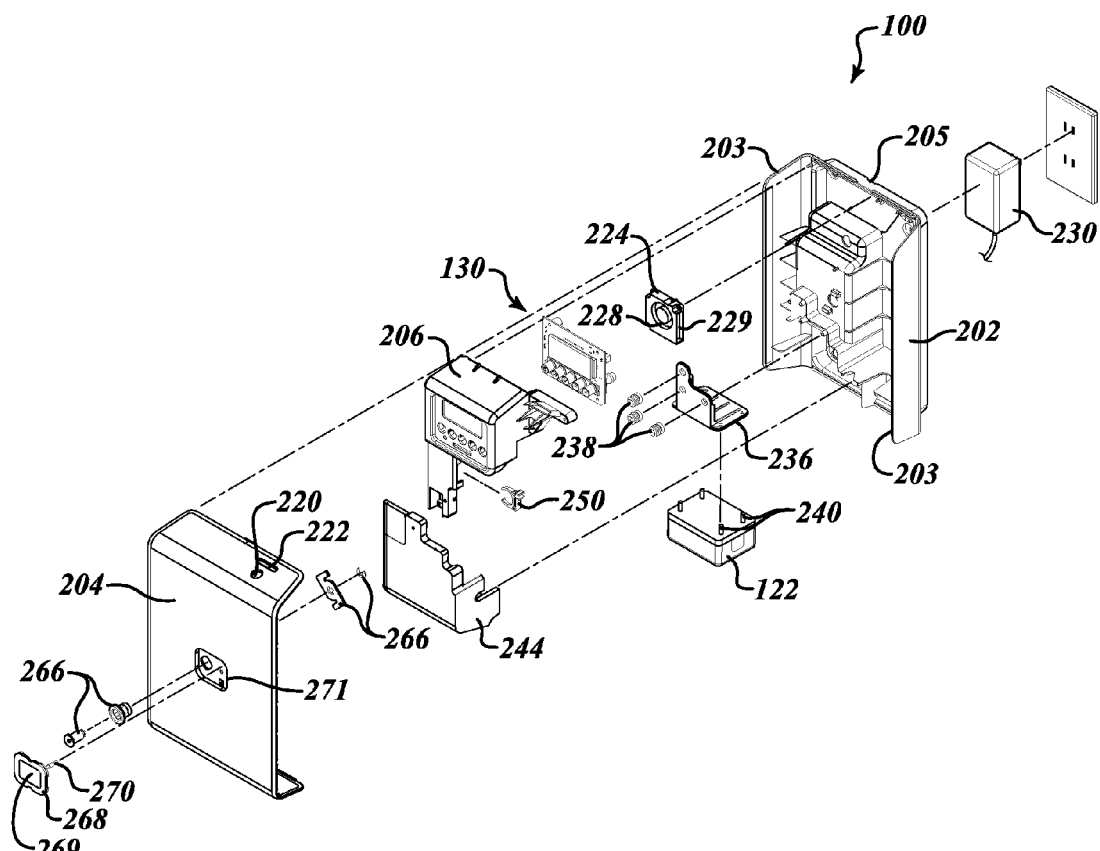
FIG. 12 is an isometric exploded view of the air treatment appliance of FIGS. 1 and 2.

Further details of the air treatment appliance 100 and components thereof will be appreciated by those of ordinary skill in the relevant art upon a review of the exploded view of the air treatment appliance 100 shown in FIG. 12.

In the present disclosure, the outlet 132 of the cartridge 102 and hence of the appliance 100 permit atomized liquid generated within the cartridge 102 to flow directly into a space to be treated. However, the appliance 100 could alternatively direct diffused or aerosolized compound into an air transport or distribution system instead. The air transport system might include ductwork or other avenues that would permit the diffused or aerosolized compound to be dispersed into a remotely located space or a plurality of remotely located spaces. Thus, the appliance 100 could be used to diffuse and disperse liquid throughout an entire building, for example, through an existing HVAC system.

It may also be noted that the air treatment appliances 100, removable cartridges 102 and components disclosed herein may include operational control via controller 130 for varying the pressure, velocity and/or timing of operation of the onboard pump assembly 122 to provide air flow through the cartridge 102. In addition to using the controller 130 to alter the amount of liquid diffused or aerosolized by the appliance 100 and the corresponding degree of treatment of a space, the characteristics of the liquid to be diffused may also affect the amount of liquid diffused and the degree of treatment. For example, more viscous liquids may diffuse more slowly. The density of the liquid may also affect the degree of treatment provided. These characteristics of the liquid 120 in the cartridge 102 may also be taken into account when setting controls regarding the function and operation of the appliances 100 into which the cartridges 102 are received.

Again, although certain specific details are set forth in order to provide a thorough understanding of various disclosed embodiments, one skilled in the relevant art will recognize that embodiments may be practiced without one or more of these specific details Moreover, aspects and features of the various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheetare incorporated herein by reference, in their entirety. Aspects of the embodiments can be modified, if necessary to employ features, structures, functionality or concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An air treatment appliance, comprising:
 a removable cartridge containing a liquid compound to be aerosolized and including a cartridge outlet through which the aerosolized compound is discharged;

a pump operatively coupled to the removable cartridge to supply air to the removable cartridge to generate the aerosolized compound from the liquid compound contained in the removable cartridge;

a controller operatively coupled to the pump for controlling the pump to supply the air to the removable cartridge to generate the aerosolized compound and discharge the aerosolized compound from the cartridge outlet; and an appliance housing that accommodates the removable cartridge, the pump and the controller within an internal cavity thereof, the appliance housing including a base, a cover coupled to the base to define the internal cavity, and an inner sub-housing located within the internal cavity, the inner sub-housing coupled to the base to collectively define a passageway having an air outlet positioned to discharge a flow of air across a path of the aerosolized compound discharged from the cartridge outlet during operation, wherein the inner sub-housing includes a discharge nozzle which defines a terminal end of the passageway and includes the air outlet, the discharge nozzle oriented to discharge the flow of air oblique to the path of the aerosolized compound discharged from the cartridge outlet, and wherein the inner sub-housing further includes a tongue having an alignment groove for receiving a stem of the removable cartridge which contains the cartridge outlet and for assisting in aligning the cartridge outlet and the path of the aerosolized compound with the air outlet of the discharge nozzle of the inner sub-housing.

2. The air treatment appliance of claim 1, further comprising:

a fan device positioned within a compartment of the appliance housing formed between the base and the inner sub-housing, the fan device including a fan intake and a fan outlet arranged to draw in air from the compartment and move air through the passageway leading to the air outlet that is positioned to discharge the flow of air across the path of the aerosolized compound discharged from the cartridge outlet during operation.

3. The air treatment appliance of claim 2 wherein at least some functional electronics of the controller are located within the compartment of the appliance housing formed between the base and the inner sub-housing, and wherein the fan intake is arranged to draw in air from across said functional electronics of the controller.

4. The air treatment appliance of claim 1, further comprising:

a power adapter unit connected to a power outlet of a wall, and wherein the base of the appliance housing defines a power adapter cavity sized and shaped to accommodate the power adapter unit and to conceal the power adapter unit when the air treatment appliance is fixed to the wall.

5. The air treatment appliance of claim 1, further comprising:

a pump mount arrangement that couples the pump to the appliance housing, the pump mount arrangement including a pump bracket and a plurality of groupings of isolators arranged in orthogonal planes to suppress vibrations of the pump in multiple directions.

6. The air treatment appliance of claim 5 wherein the pump bracket suspends the pump within a pump cavity located at a lower end of the appliance housing.

7. The air treatment appliance of claim 1 wherein the base and the cover of the appliance housing collectively define a pump cavity to accommodate the pump, and wherein the air treatment appliance further comprises a sound deadening or muffling device positioned within the pump cavity to substantially fill a void between the pump and the appliance housing.

8. The air treatment appliance of claim 7 wherein the sound deadening or muffling device comprises a compliant material formed in a shape that corresponds to the void between the pump and the appliance housing.

9. The air treatment appliance of claim 1 wherein the base of the appliance housing includes a back and opposing sidewalls, and wherein upper and lower edges of the back and a peripheral edge of each of the opposing sidewalls include a plurality of indentations to receive corresponding projections of the cover to join the base and the cover together without separate fasteners.

10. An air treatment appliance, comprising:

a removable cartridge containing a liquid compound to be aerosolized and including a cartridge outlet through which the aerosolized compound is discharged, the removable cartridge including a base receptacle having one or more alignment indentations formed in a side thereof;

a pump operatively coupled to the removable cartridge to supply air to the removable cartridge to generate the aerosolized compound from the liquid compound contained in the removable cartridge;

a controller operatively coupled to the pump for controlling the pump to supply the air to the removable cartridge to generate the aerosolized compound and discharge the aerosolized compound from the cartridge outlet; and an appliance housing that accommodates the removable cartridge, the pump and the controller within an internal cavity thereof, the appliance housing including a base and a cover coupled to the base to define the internal cavity, and the base of the appliance housing including a back and opposing sidewalls with one or more corresponding alignment projections which nest with the alignment indentations of the removable cartridge.

11. An air treatment appliance, comprising:

a removable cartridge containing a liquid compound to be aerosolized and including a cartridge outlet through which the aerosolized compound is discharged;

a pump operatively coupled to the removable cartridge to supply air to the removable cartridge to generate the aerosolized compound from the liquid compound contained in the removable cartridge;

a controller operatively coupled to the pump for controlling the pump to supply the air to the removable cartridge to generate the aerosolized compound and discharge the aerosolized compound from the cartridge outlet;

an appliance housing that accommodates the removable cartridge, the pump and the controller within an internal cavity thereof, the appliance housing including a base and a cover coupled to the base to define the internal cavity; and a conduit assembly that couples an air outlet of the pump to an air inlet of the removable cartridge, the conduit assembly including a conduit fitting and a conduit with one or more corrugated sections to facilitate routing of the conduit between the air outlet of the pump and the air inlet of the removable cartridge, the conduit fitting including a seal member having a plurality of resilient projections at a terminal end thereof for sealingly engaging the air inlet of the removable cartridge, a stem for mating with a terminal end of the conduit, and a locking device for locking the conduit fitting and the conduit to the removable cartridge.

12. An air treatment appliance, comprising:
a removable cartridge containing a liquid compound to be aerosolized and including a cartridge outlet through which the aerosolized compound is discharged;
a pump operatively coupled to the removable cartridge to supply air to the removable cartridge to generate the aerosolized compound from the liquid compound contained in the removable cartridge;
a controller operatively coupled to the pump for controlling the pump to supply the air to the removable cartridge to generate the aerosolized compound and discharge the aerosolized compound from the cartridge outlet;
an appliance housing that accommodates the removable cartridge, the pump and the controller within an internal cavity thereof, the appliance housing including a base and a cover coupled to the base to define the internal cavity; and
a conduit that couples an air outlet of the pump to an air inlet of the removable cartridge, the conduit including a unitary structure comprising one or more corrugated sections to facilitate routing of the conduit between the air outlet of the pump and the air inlet of the removable cartridge, a plurality of resilient projections at a terminal end thereof for sealingly engaging the air inlet of the removable cartridge, and a locking device for locking the conduit to the removable cartridge.

13. The air treatment appliance of claim 12 wherein the locking device includes a grip portion for manipulating the locking device and for assisting in installing the removable cartridge in the appliance housing and removing the removable cartridge from the appliance housing.

14. An air treatment appliance, comprising:
a removable cartridge containing a liquid compound to be aerosolized and including a cartridge outlet through which the aerosolized compound is discharged;
a pump operatively coupled to the removable cartridge to supply air to the removable cartridge to generate the aerosolized compound from the liquid compound contained in the removable cartridge;
a controller operatively coupled to the pump for controlling the pump to supply the air to the removable cartridge to generate the aerosolized compound and discharge the aerosolized compound from the cartridge outlet;
an appliance housing that accommodates the removable cartridge, the pump and the controller within an internal cavity thereof, the appliance housing including a base and a cover coupled to the base to define the internal cavity;
a supplemental power source; and
a caddy for the supplemental power source, the caddy removably positioning the supplemental power source within the appliance housing and including finger grips projecting from an end thereof for assisting in removal of the supplemental power source from the appliance housing.

15. An air treatment appliance, comprising:
a removable cartridge containing a liquid compound to be aerosolized and including a cartridge outlet through which the aerosolized compound is discharged;
a pump operatively coupled to the removable cartridge to supply air to the removable cartridge to generate the aerosolized compound from the liquid compound contained in the removable cartridge;
a controller operatively coupled to the pump for controlling the pump to supply the air to the removable cartridge to generate the aerosolized compound and discharge the aerosolized compound from the cartridge outlet; and
an appliance housing that accommodates the removable cartridge, the pump and the controller within an internal cavity thereof, the appliance housing including a base and a cover coupled to the base to define the internal cavity, and the base of the appliance housing including a back having an arrangement of mounting apertures for securing the appliance housing to a wall, or alternatively to an appliance stand.

16. An air treatment appliance, comprising:
a removable cartridge containing a liquid compound to be aerosolized and including a cartridge outlet through which the aerosolized compound is discharged;
a pump operatively coupled to the removable cartridge to supply air to the removable cartridge to generate the aerosolized compound from the liquid compound contained in the removable cartridge;
a controller operatively coupled to the pump for controlling the pump to supply the air to the removable cartridge to generate the aerosolized compound and discharge the aerosolized compound from the cartridge outlet; and
an appliance housing that accommodates the removable cartridge, the pump and the controller within an internal cavity thereof, the appliance housing including a base, a cover coupled to the base to define the internal cavity, and a lock assembly coupled to the cover for locking the cover directly to one or more catch members formed integrally with the base of the appliance housing.

17. The air treatment appliance of claim 16 wherein the lock assembly includes a retaining ring having an upstanding tab to assist in installation and removal of the retaining ring.

18. The air treatment appliance of claim 16 wherein the cover includes a separate sub-cover for concealing the lock assembly, the sub-cover being removably secured to the cover via an arrangement of integral coupling members and a flexible lanyard.

19. An air treatment appliance, comprising:
a removable cartridge containing a liquid compound to be aerosolized and including a cartridge outlet through which the aerosolized compound is discharged;
a pump operatively coupled to the removable cartridge to supply air to the removable cartridge to generate the aerosolized compound from the liquid compound contained in the removable cartridge;
a controller operatively coupled to the pump for controlling the pump to supply the air to the removable cartridge to generate the aerosolized compound and discharge the aerosolized compound from the cartridge outlet;
an appliance housing that accommodates the removable cartridge, the pump and the controller within an internal cavity thereof, the appliance housing including a base and a cover coupled to the base to define the internal cavity, each of the cover and the base of the appliance housing including a respective lanyard mount formed integrally therewith; and a lanyard connecting the cover to the base via the lanyard mounts.

\* \* \* \* \*